United States Patent
Wang et al.

(10) Patent No.: US 7,163,790 B2
(45) Date of Patent: Jan. 16, 2007

(54) PARALLEL POLYMORPHISM SCORING BY AMPLIFICATION AND ERROR CORRECTION

(75) Inventors: Yan Wang, San Francisco, CA (US); Michael Finney, San Francisco, CA (US); Fan Chen, Alameda, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 541 days.

(21) Appl. No.: 10/306,828

(22) Filed: Nov. 27, 2002

(65) Prior Publication Data

US 2003/0138830 A1 Jul. 24, 2003

Related U.S. Application Data

(60) Provisional application No. 60/334,032, filed on Nov. 28, 2001.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 536/23.1, 24.3
See application file for complete search history.

(56) References Cited

U.S. PATENT DOCUMENTS

| | | | |
|---|---|---|---|
| 4,851,331 A * | 7/1989 | Vary et al. .......... | 435/6 |
| 5,210,015 A | 5/1993 | Gelfand et al. | |
| 5,391,480 A | 2/1995 | Davis et al. | |
| 5,487,972 A | 1/1996 | Gelfand et al. | |
| 5,521,301 A | 5/1996 | Wallace et al. | |
| 5,545,552 A | 8/1996 | Mathur | |
| 5,639,611 A * | 6/1997 | Wallace et al. .......... | 435/6 |
| 5,736,626 A * | 4/1998 | Mullah et al. .......... | 536/25.3 |
| 5,759,772 A * | 6/1998 | Kirkpatrick et al. .......... | 435/6 |
| 5,848,717 A | 12/1998 | Bosl et al. | |
| 5,851,770 A | 12/1998 | Babon et al. | |
| 5,955,268 A * | 9/1999 | Granados et al. .......... | 435/6 |
| 6,001,567 A | 12/1999 | Brow et al. | |
| 6,120,992 A | 9/2000 | Wagner, Jr. | |
| 6,174,670 B1 * | 1/2001 | Wittwer et al. .......... | 435/6 |
| 6,248,526 B1 | 6/2001 | Weimer | |
| 6,627,424 B1 * | 9/2003 | Wang .......... | 435/194 |
| 2002/0142336 A1 | 10/2002 | Smith et al. | |
| 2003/0036073 A1 * | 2/2003 | Saba .......... | 435/6 |
| 2004/0053279 A1 * | 3/2004 | Decker et al. .......... | 435/6 |

FOREIGN PATENT DOCUMENTS

EP 0070685 A2 1/1983

OTHER PUBLICATIONS

Lu et al., PNAS 80 : 4639-4643 (Aug. 1983).*
Newton et al., Nucleic Acids Research 17(7) : 2503-2516 (1989).*
Wittwer et al., Clinical Chemistry 39(5) : 804-809 (1993).*
Pastinen et al., A System for Specific, High-throughput Genotyping by Allele-specific Primer Extension on Microarrays. Genome Research 10 : 1031-1042 (2000).*
Cardullo et al., "Detection of nucleic acid hybridization by nonradiative fluorescence resonance energy transfer", *Proc. Natl. Acad. Sci.* 85: 8790-8794 (1988).
Wang et al., "Large-Scale Identification, Mapping, and Genotyping of Single-Nucleotide Polymorphisms in the Human Genome", *Science* 280: 1077-1082 (1998).
Saiki et al., "Enzymatic Amplification of β-globin Genomic Sequences and Restriction Site Analysis for Diagnosis of Sickle Cell Anemia" *Science* 230: 1350-1354 (1985).
Shumaker et al., "Mutation Detection by Solid Phase Primer Extension", *Human Mutation* 7: 346-354 (1996).
Ugozzoli et al., "Detection of Specific Alleles by Using Allele-Specific Primer Extension Followed by Capture on Solid Support", *GATA* 9:4: 107-112 (1992).
Chen et al., "Homogeneous genotyping assays for single nucleotide polymorphisms with fluorescence resonance energy transfer detection", Genetic Analysis: *Biomolecular Engineering* 14: 157-163 (1999).
Bi, W., et al., "Detection of known mutation by proof-reading PCR," *Nucleic Acids Research*, 1998, vol. 26, No. 12, pp. 3073-3075.

* cited by examiner

*Primary Examiner*—Ethan Whisenant
(74) *Attorney, Agent, or Firm*—Townsend and Townsend and Crew LLP

(57) ABSTRACT

This invention provides a method of detecting polymorphisms, e.g., single nucleotide polymorphisms (SNPs), by amplification and error correction. The invention encompasses methods of performing amplification and error correction using an improved generation of nucleic acid polymerases, and methods of multiplexing the assay. The improvement to the polymerases is the joining of a sequence-non-specific nucleic-acid-binding domain to the enzyme in a manner that enhances the ability of the enzyme to bind and catalytically modify the nucleic acid.

31 Claims, 2 Drawing Sheets

SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:PCR forward Primer F1

<400> SEQUENCE: 1

```
aggcgcttct ccgtg                                                    15

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:PCR reverse
      Primer R1

<400> SEQUENCE: 2
ctccagcgac ttcttgc                                                  17

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:PCR 3'
      base-labeled forward Primer F2
<220> FEATURE:
<221> NAME/KEY: modified_base
<222> LOCATION: (15)
<223> OTHER INFORMATION: n = c with carboxyfluorescein (FAM) dye
      attached at the 5 position through a linker

<400> SEQUENCE: 3
aggcgcttct ccgtn                                                    15

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:PCR reverse
      Primer R2

<400> SEQUENCE: 4
atgtcctttc ccaaacccat                                               20

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:PCR 3'
      base-labeled forward Primer F3
<220> FEATURE:
<221> NAME/KEY: modified_base
<222> LOCATION: (15)
<223> OTHER INFORMATION: n = t labeled with Bodipy R6G (BR6G) linked to
      the methyl group via a 6-carbon linker

<400> SEQUENCE: 5
aggcgcttct ccgtn                                                    15
```

PARALLEL POLYMORPHISM SCORING BY AMPLIFICATION AND ERROR CORRECTION

CROSS-REFERENCES TO RELATED APPLICATIONS

This application claims the benefit of U.S. provisional application No. 60/334,032, filed Nov. 28, 2001, which is incorporated by reference herein.

FIELD OF THE INVENTION

This invention provides a method of detecting polymorphisms, e.g., single nucleotide polymorphisms (SNPs) by amplification and error correction. The invention encompasses methods of performing amplification and error correction using an improved generation of nucleic acid polymerases, and methods of multiplexing the assay. The improvement to the polymerases is the joining of a sequence-non-specific nucleic-acid-binding domain to the enzyme in a manner that enhances the ability of the enzyme to bind and catalyticly modify the nucleic acid.

BACKGROUND OF THE INVENTION

The smallest possible difference between two DNA sequences is a change of a single base, a Single Nucleotide Polymorphism or SNP. Such differences are common in the human population, occurring roughly one every 1000 bases between any two unrelated individuals. Some SNPs have medically important consequences, while others are silent but may be useful as markers to study genetic transmission of traits.

A number of methods have been developed to score SNPs, including allele-specific hybridization, electrophoretic DNA sequencing, single-nucleotide extension using labeled chain terminators, the "Invader" assay (Third Wave Technologies, Madison Wis.), mass spectrometry, the 5' nuclease, assay (Taqman; see below), etc. All of these methods entail assays that are either difficult or expensive to develop, or difficult or expensive to perform.

It will be appreciated that while SNPs are common, it is at times advantageous to score other polymorphisms such as insertions, deletions, rearrangements or sequence alterations involving more than one base. SNP scoring has been emphasized in the literature because it is the most difficult case, but most methods capable of scoring SNPs are also capable of scoring additional types of polymorphisms.

One of the known assays for detecting single-base differences in DNA samples uses an exonuclease specific for mismatched bases (see, e.g., U.S. Pat. No. 5,391,480). In general, such an assay involves labeling the 3' nucleotide in a primer with a fluorescent marker. The labeled oligonucleotide is hybridized to an unknown DNA sample. If the 3' nucleotide (the query position) of the oligonucleotide is complementary to the corresponding nucleotide in the hybridized DNA, it will be insensitive to nuclease; if there is a mismatch it will be sensitive to nuclease and will be cleaved. For example, in a PCR reaction, the query position corresponds to the 3' end of one of the two primers. This primer is synthesized in two versions (1 and 2), one complementary to each of the two expected versions of a SNP (SNP versions 1 and 2, respectively). The 3' nucleotides of primers 1 and 2 are labeled with distinguishable fluors. The polymerase used for the PCR is one capable of excising mismatched 3' nucleotides (an "error-correcting" or "3' exonuclease-activity-containing" polymerase). If the input template contains SNP version 1, then primer 2 will at some frequency anneal to an amplicon containing SNP version 1 and the 3' nucleotide will be clipped off by the error-correcting activity of the polymerase. Clipped-off fluorescent nucleotides are detected by a decrease in fluorescence polarization (FP). At the same time, primer 1, which is fully complementary to SNP version 1, will at some frequency anneal to an amplicon containing SNP version 1 and be extended to full amplicon length. The extended primer then becomes insensitive to further attack by nuclease. Thus, if SNP version 1 is present, there will be a decrease in FP for the fluor linked to primer 2; if SNP version 2 is present, there will be a decrease in FP for the fluor linked to primer 1; if both SNP versions are present (as in a heterozygote), then there will be a decrease in FP for both fluors, but to a smaller extent for each.

Commercially-available polymerases such as Pfu are capable of extending a labeled nucleotide if it is correctly matched and clipping it if it is mismatched. The procedure is also distinct from the "Taqman" assay (see, e.g., U.S. Pat. Nos. 5,210,015 and 5,487,972), which uses the 5'-3' nuclease activity of some thermostable polymerases.

There are a number of problems and deficiencies with this method, however. First, known error-correcting polymerases, such as the *Pyrococcus* genus family B polymerases, are ill-suited to amplification of sequences directly from genomic DNA. The processivity of the polymerases is too low to reliably complete a full-length copy of an amplicon in a single round. Thus, completion of a full length copy must rely on hybridization of the partial copies to a suitable template in the reaction mix, and therefore only occurs if the template concentration is relatively high. This creates a problem, because it is preferable to use low amounts of genomic DNA in a PCR reaction in order to allow use of DNA that is not highly purified; and to reduce the amount of non-specific DNA, which can lead to side reactions, present in the reaction. The prior art protocol is therefore conventionally performed by 1) pre-amplifying a region containing the SNP site using unlabeled primers and Taq or other polymerase capable of amplifying single copies, 2) purifying the amplified DNA, 3) re-amplifying with labeled primers and an error-correcting polymerase, and 4) detecting whether error correction has occurred.

Second, the methods used for scoring whether error correction has occurred (and therefore what versions of an SNP are present in the original sample) are inadequate for low cost and high throughput. Given the cost of reagents and disposables, and the amortized cost of equipment and space, it is exceedingly difficult to run a PCR for less than 10–20 US cents. Yet, for many applications, SNP scoring is not economical unless it can be done for 1 US cent per locus. Therefore, it is necessary to score at least ten and perhaps many more SNPs per PCR. Assays based on scoring with FP can score no more than 1 or 2 SNPs per PCR.

The current invention meets the need for an economical SNP assay that can be performed using small amounts of genomic DNA. Here, we describe an error-correction SNP assay capable of robust operation from small amounts of genomic DNA and several methods for parallelizing this assay for low-cost, high throughput operation.

The processivity of a polymerase, i.e., the amount of product generated by the enzyme per binding event, can be enhanced by increasing the stability of the modifying enzyme/nucleic acid complex. Co-pending U.S. application Ser. No. 09/870,353 and WO01/92501 disclose modified polymerases that have increased processivity that is achieved by joining a sequence-non-specific double-stranded nucleic acid binding domain to the enzyme, or its catalytic domain. Among the modified polymerases disclosed are error-correcting Family B polymerases, which typically are used in the current invention.

BRIEF SUMMARY OF THE INVENTION

The current invention provides methods of identifying a polymorphism using an error-correcting assay. A first method comprises: (a) contacting a target nucleic acid comprising a query sequence with a probe oligonucleotide under conditions in which the probe specifically hybridizes to the target nucleic acid, wherein the 3' nucleotide of the probe is a labeled query nucleotide and the probe oligonucleotide is attached to a discrete surface location, e.g., in a microarray, by a linkage that does not include the 3' nucleotide; (b) providing an error-correcting polymerase; (c) incubating the assay under conditions in which the probe is extended by the polymerase, wherein the labeled query nucleotide is cleaved from the probe when mismatched with the query sequence; and (d) detecting the amount of probe in the discrete location that has been cleaved.

A second method comprises: (a) contacting a target nucleic acid comprising a query sequence with a probe oligonucleotide under conditions in which the probe specifically hybridizes to the target nucleic acid, wherein the 3' nucleotide of the probe is a labeled query nucleotide; (b) providing an error-correcting polymerase; (c) incubating the assay under conditions in which the probe is extended by the polymerase, wherein the labeled query nucleotide is cleaved from the probe when mismatched with the query sequence; (d) providing a capture oligonucleotide attached to a discrete location and complementary to the product of the extended probe; (e) allowing the product of the extended probe the opportunity to hybridize with the capture oligonucleotide; and (f) determining the amount of label associated with the discrete location.

A third method comprises: (a) contacting a target nucleic acid comprising at least two query sequences with at least two probe oligonucleotides under conditions in which the probes specifically hybridize to the target nucleic acid, wherein the 3' nucleotides of the probes are labeled query nucleotides; (b) providing an error-correcting polymerase; (c) incubating the assay under conditions in which the probes are extended by the polymerase, wherein the labeled query nucleotides are cleaved from the probe when mismatched with the query sequences; (d) separating the products of the extended probes electrophoretically; and (e) determining the amount of label associated with the products of each extended probe.

A fourth method comprises: (a) contacting a target nucleic acid comprising a query sequence with a probe oligonucleotide under conditions in which the probe specifically hybridizes to the target nucleic acid, wherein the 3' nucleotide of the probe is a labeled query nucleotide; (b) providing an error-correcting polymerase comprising at least two heterologous domains, wherein a first domain that is a sequence-non-specific nucleic-acid-binding domain is joined to a second domain that is a polymerase domain, wherein the sequence non-specific nucleic-acid-binding domain: (i) binds to double-stranded nucleic acid, and (ii) enhances the processivity of the polymerase compared to an identical polymerase not having the sequence non-specific nucleic-acid-binding domain fused to it; (c) incubating the assay under conditions in which the probe is extended by the polymerase, wherein the labeled query nucleotide is cleaved from the probe when mismatched with the query sequence; and (d) detecting the amount of cleaved probe or cleaved label.

In another embodiment, the probe oligonucleotide is one of two primers in a polymerase chain reaction.

The target nucleic acid can be obtained using a PCR performed with two unlabeled primers, wherein the query sequence is not present in either of the two primers; and further, wherein the PCR reaction is contacted with the probe oligonucleotide during amplification. The 3' query nucleotide can also be labeled with a quencher.

In another embodiment, the oligonucleotide probe can be complementary to a region in the amplicon that does not comprise the two primers. Additionally, the method can be performed using with a second probe oligonucleotide. The method of claim 1, further comprising a second probe oligonucleotide.

The 3' end label of the assay can be labeled with a fluorescent label and the extended product is then assayed for incorporation of the fluorescent label. The 3' end can also be labeled with a fluorescent quenching molecule and the extended product can be assayed for loss of the quencher. Alternatively, the extended product can be detected by electrophoresis and determining the presence of a fluorescent band corresponding to the extended product.

DETAILED DESCRIPTION OF THE INVENTION

Definitions

Figure 1:
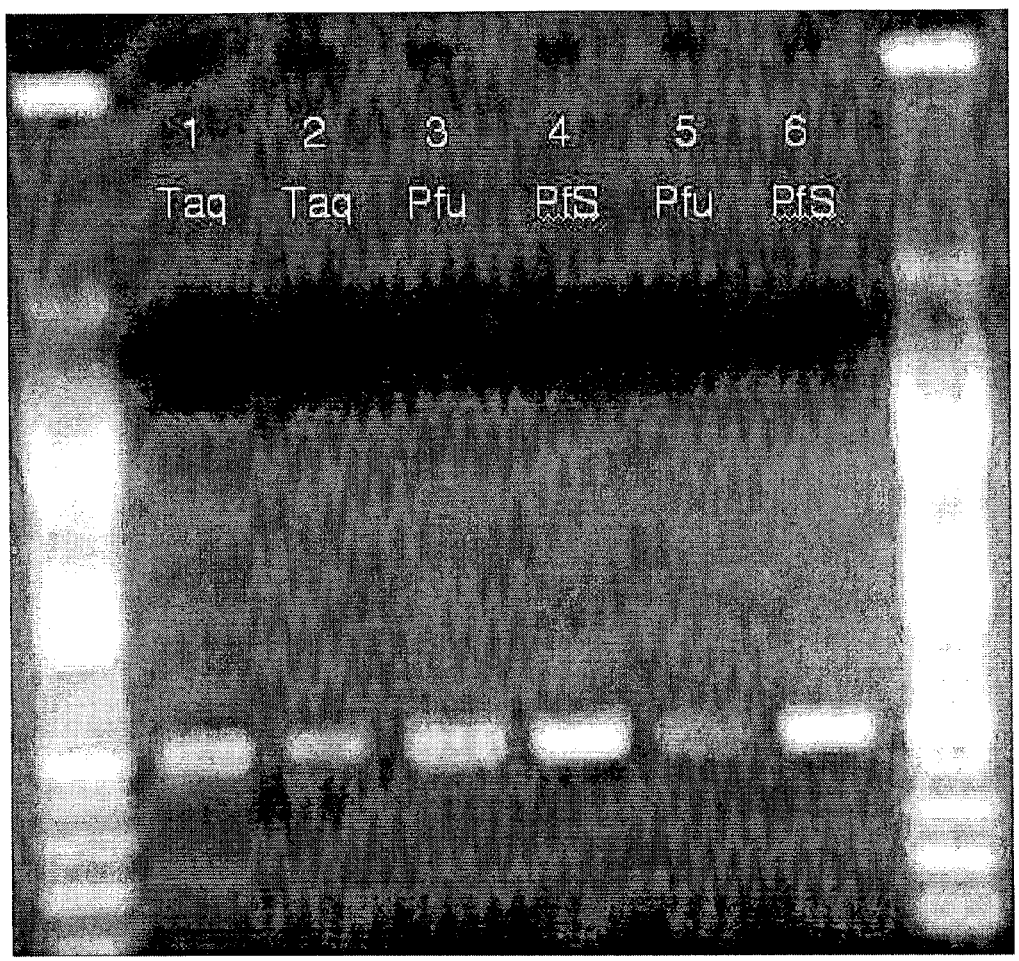
FIG. 1 shows an agarose gel of reaction products from an assay that shows that the error-correcting enzymes Pfu and PfS efficiently correct mismatched labeled bases during PCR amplification.

"Enhances" in the context of an enzyme refers to improving the activity of the enzyme, e.g., increasing the amount of product per unit enzyme per unit time.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

A "polymerase" can include an entire enzyme or a catalytic domain.

An "improved polymerase" includes a sequence-non-specific double-stranded DNA binding domain joined to the polymerase or polymerase domain. An "unimproved polymerase" or "unmodified polymerase" is a polymerase that does not have a sequence-non-specific double-stranded DNA binding domain. "Improved polymerases" are described, for example in WO01/92501.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Error-correcting activity" of a polymerase or polymerase domain refers to the 3' to 5' exonuclease proofreading activity of a template-specific nucleic acid polymerase whereby nucleotides that do not form Watson-Crick base pairs with the template are removed from the 3' end of an oligonucleotide, i.e., a strand being synthesized from a template, in a sequential manner. Examples of polymerases that have error-correcting activity include polymerases from *Pryococcusfuriosus, Thermococcus litoralis*, and *Thermotoga maritima*.

"Processivity" refers to the ability of a nucleic acid modifying enzyme to remain attached to the template or substrate and perform multiple modification reactions. Typically "processivity" refers to the number of reactions catalyzed per binding event.

"Sequence-non-specific nucleic-acid-binding domain" refers to a protein domain which binds with significant affinity to a nucleic acid, for which there is no known nucleic acid which binds to the protein domain with more than 100-fold more affinity than another nucleic acid with the same nucleotide composition but a different nucleotide sequence.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

The term "amplification reaction" refers to any in vitro means for multiplying the copies of a target sequence of nucleic acid. Such methods include but are not limited to polymerase (PCR), DNA ligase, (LCR), QβRNA replicase, and RNA transcription-based (TAS and 3SR) amplification reactions.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and *PCR Protocols: A Guide to Methods and Applications*, Innis et al., eds., 1990; Sambrook and Russell, Molecular Cloning, a Laboratory Manual (3rd ed. 2001); and Current Protocols in Molecular Biology (Ausubel et al., eds., John Wiley & Sons, Inc. 1994–1997, 2001 version).

"Long PCR" refers to the amplification of a DNA fragment of 5 kb or longer in length. Long PCR is typically performed using specially-adapted polymerases or polymerase mixtures (see, e.g., U.S. Pat. Nos. 5,436,149 and 5,512,462) that are distinct from the polymerases conventionally used to amplify shorter products.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12–25 nucleotides, in length. The length and sequences of primers for use in PCR can be designed based on principles known to those of skill in the art, see, e.g., Innis et al., supra.

A "capture oligonucleotide" refers to an oligonucleotide attached to a discrete location, which is used for hybridizing to polynucleotides present in solution and causing them to remain in association with the discrete location.

An "oligonucleotide" refers to natural or synthetic chemical substances that are capable of hybridizing with polynucleotides, or otherwise substituting for natural polynucleotides in enzymatic reactions. Oligonucleotides include polymers containing non-natural monomers such as modified bases and peptide nucleic acid (PNA) monomers.

A "probe" refers to a polynucleotide sequence capable of hybridization to a polynucleotide sequence of interest and allows for the detecting of the polynucleotide sequence of choice. For example, "probes" can comprise polynucleotides linked to fluorescent or quenching reagent, thereby allowing for the detection of these reagents.

The term "subsequence" refers to a sequence of nucleotides that are contiguous within a second sequence but does not include all of the nucleotides of the second sequence.

A "target" or "target sequence" refers to a single or double stranded polynucleotide sequence sought to be amplified in an amplification reaction. Two target sequences are different if they comprise non-identical polynucleotide sequences.

A "temperature profile" refers to the temperature and lengths of time of the denaturation, annealing and/or extension steps of a PCR reaction. A temperature profile for a PCR reaction typically consists of 10 to 60 repetitions of similar or identical shorter temperature profiles; each of these shorter profiles typically define a two step or three-step PCR reaction. Selection of a "temperature profile" is based on various considerations known to those of skill in the art, see, e.g., Innis et al., supra. In a long PCR reaction as described herein, the extension time required to obtain an amplification product of 5 kb or greater in length is reduced compared to conventional polymerase mixtures.

Amplification or PCR "sensitivity" refers to the ability to amplify a target nucleic acid that is present in low copy number. "Low copy number" refers to $10^5$, often $10^4$, $10^3$, $10^2$, or fewer, copies of the target sequence in the nucleic acid sample to be amplified.

A "template" refers to a double stranded polynucleotide sequence that comprises the polynucleotide to be amplified, flanked by primer hybridization sites. Thus, a "target template" comprises the target polynucleotide sequence flanked by hybridization sites for a 5' primer and a 3' primer.

The term "query" position refers to the target polymorphic nucleotide or other polymorphism targeted by an assay of the invention.

"Multiplex amplification" refers to amplification of multiple polynucleotide fragments in the same reaction (see, e.g., PCR Primer, a Laboratory Manual (Dieffenbach, ed. 1995) Cold Spring Harbor Press, pages 157–171.

A "polymorphism" is an allelic variant. Polymorphisms can include single nucleotide polymorphisms as well as simple sequence length polymorphisms. A polymorphism can be due to one or more nucleotide substitutions at one allele in comparison to another allele or can be due to an insertion or deletion.

A "solid support" refers to any material to which an oligonucleotide can be attached or any material that can be modified so that an oligonucleotide can be attached to it. Illustrative solid surfaces or solid supports include, e.g., nitrocellulose, nylon, glass, quartz, polystyrene, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface or solid support is porous, various pore sizes may be employed depending upon the nature of the system.

Introduction

The invention provides an error-correction polymorphism assay PACE, for Polymorphism Assay by Correction of Errors, which is capable of robust operation from small amounts of genomic DNA and several schemes for parallelizing this assay for low-cost, high throughput operation. The assay is typically performed using an improved error-correcting polymerase that comprises a thermostable sequence-nonspecific double-stranded DNA-binding domain, e.g., Sso7d, attached to the polymerase, or a catalytic domain of the polymerase, which increases the processivity of the polymerase.

The description of the invention often refers to SNP assays as examples of polymorphism assays, but it will be appreciated that more complex polymorphisms can be detected by PACE. As long as enough of a labeled primer is complementary to a template sequence to allow priming, and the 3' labeled end of the primer is complementary to one allele of a polymorphism, but not complementary to another allele, then PACE can distinguish between those two alleles. For instance, in the case of a deletion, e.g., from 1 to approximately 5000 bases, one labeled oligonucleotide may be complementary to the undeleted DNA, with its 3' end corresponding to the first nucleotide that is different in the deletion allele; the other labeled oligonucleotide may be identical to the first, except that the 3' end is complementary to the sequence found in the deletion allele. Similar logic can be used to design PACE primers to detect insertions, inversions, and multi-base sequence changes.

Polymerases with 3' nuclease activity are suitable for the assays. Such polymerases include *Pyrococcus* polymerases such as Pfu, Pho, Pab, Pko, Pgl etc. and *Thermococcus* polymerases such as Tli (Vent), which are sufficiently thermostable to be suitable for PCR. Other polymerases that are not thermostable may also be used. For example, *E. coli* PolA has 3' to 5' exonuclease activitiy and could be used in an embodiment where the error correcting step is not performed at high termperatures. Engineered polymerases with 3' nuclease activity that have at least 60% amino acid similarity to any natural error-correcting polymerase may also be used. Typically, these polymerases are modified by fusion with thermostable sequence-nonspecific double-stranded DNA-binding proteins such as Sso7d for use in the assay.

In a particular embodiment, the polymerase is a fusion of Sso7d to the C-terminus of Pfu polymerase, an enzyme referred to as Pfu-Sso7d or "PfS". Example 1 shows that Pfs performs an error-correcting assay including amplification directly from genomic DNA of low copy number templates in circumstances where Pfu does not work.

Example 2 shows that amplification with PfS distinguishes two different templates with a single nucleotide difference between them, as well as a 50:50 mixture of the two.

PACE Assays

This invention uses the error-correcting SNP assay for parallel methods of scoring single nucleotide polymorphisms, by modifying it so that it can be highly multiplexed. Rather than multiplexing by increasing the number of distinguishable fluorescent colors, the multiplex reactions of the current invention use only a small number of colors in a large number of discrete locations.

Assay 1: Amplification in the Presence of a Labeled Array.

An important concept in this assay is to employ oligonucleotides attached to discrete locations, where the attachment method permits a free 3' end to serve as a potential substrate for the 3' nuclease activity of a polymerase. The 3' nucleotide is labeled, and the assay as performed surveys the discrete locations to determine whether a significant fraction, i.e., more than in a negative control, of the 3' nucleotides attached to a particular location have been clipped off.

A number of other features can also be incorporated to further improve the assay. These optional features include, but are not limited to, the following:

1) A PCR is performed in solution, using two unlabeled oligonucleotide primers, where the query position occurs within the amplicon but is not found in either primer;

2) A labeled (probe) oligonucleotide containing the labeled query position as its 3' nucleotide is attached to a discrete surface location by a linkage that does not include the 3' nucleotide (i.e., the 3' nucleotide is free to participate in enzymatic reactions). For instance, the labeled oligonucleotide can be attached by a functional group on its 5' end. The probe is long enough to hybridize to an amplicon in solution that comprises the query position. The probe is typically at least 12–14 nucleotides in length, but can be longer, e.g., 25–30 nucleotides in length depending on the $T_M$. As appreciated by one of skill in the art, new technologies, e.g., minor groove binders (MGB) from Synthetic Genetics can increase the affinity so that the probe can also be about 10 bases in length.

3) The surface location is exposed to the PCR while the reaction is proceeding. When the unlabeled amplicon reaches sufficient concentration, it will anneal with the probe oligonucleotide, allowing the probe oligonucleotide to be extended either with or without error-correction of its 3' end.

4) The discrete surface location may be on any solid support. Typically, the discrete location is a spot on a microarray, such as is commonly constructed on a glass slide with a flat or porous surface, or is a fluorescently-labeled bead, such as the polystyrene beads commercially available from Luminex (Austin Tex.) or which have been developed by the Quantum Dot Corporation of Hayward Calif., or such as described by M. Han et al. ("Quantum dot tagged microbeads for multiplex coding of biomolecules." Nature Biotechnology, 19:7, 631–635, 2001).

5) The label on the 3' query nucleotide of the probe oligonucleotide is a quencher, and the corresponding fluor is attached to the probe oligo somewhere close to, e.g., within about 25 or 30 bases, preferably about 10 bases, but separate from the 3' nucleotide. The quencher can be a non-fluorescent molecule such as DABCYL. The purpose of this is to make the unreacted probe oligonucleotide have a low fluorescence due to the quencher, so that even small increases in fluorescence, resulting from a small amount of clipping of the 3' nucleotide, will be detectable.

6) Specificity of the assay is increased by making the probe complementary to an internal sequence. Specifically, the unlabeled amplification primers (optional feature 1) can be designed so as to amplify a significant amount of sequence not present in either primer—for instance, at least 3 and as many as 15 or more bases, e.g., 50, 100, 500, 1000, 5000 or more bases. At least part of the probe, i.e., a subsequence of the probe, is complementary to the sequence not present in either primer. The subsequence of the probe not complementary to either primer is increased until the probe oligonucleotides are functionally specific for a true template-derived amplicon, and not affected by a primer-dimer or similar artifact. Taqman-type cleavage of the probe is not an issue if a polymerase with no 5'-3' exonuclease activity is used (e.g., *Pyrococcus*-type polymerases). The probe sequence is designed to discriminate between other amplicons that may be present in the reaction, i.e., it will hybridize to one amplicon and not to the others. Exemplary hybridization conditions are typically compatible with amplification reactions, e.g., hybridization can be performed at 50 mM KCl, 10 mM Tris pH8.5, 1.5 mM $Mg^{++}$ at a temperature that is usually between 60° C. and 72° C.

7) At least two probe oligonucleotides are employed. They can be in a single discrete location and distinguished from each other by means of color, or they can be in separate discrete locations.

8) For highest confidence, four probe oligonucleotides are present, corresponding to all four possible bases in the query position. In general two bases will be expected and two will be unexpected. The unexpected bases serve as controls for the efficiency of the assay, and to score rare individuals with unexpected alleles.

9) The assays can be highly multiplexed, so that at least dozens, and perhaps many thousands of different assays can be performed together in the same solution. In parallel assays, the probe oligonucleotides are designed to have about the same $T_M$ using algorithms well known to those of skill in the art. Typically, the probes have a $T_M$ within 10° C. of one another, more often between 5° C. or 2° C. of one another.

Not all of these elements must be present for the invention to be workable. In a preferred embodiment, the assay differs from the Genome Therapeutics protocol by at least elements 1, 2, 3, and 4. The assay can be further improved by addition of elements 5, 6, 7, 8, and 9 singly or in combinations.

Assay 2: Post-Amplification Readout Using Hybridization to an Array

In this assay version, amplifications are performed, typically directly from genomic DNA, and the assay is read out, i.e., the results are determined, by hybridization to probes fixed to a discrete location on a solid support, e.g., a microarray. In general, this assay is performed by PCR amplification, where one of the primers has the polymorphic sites, e.g., an SNP site, at its 3' end, and that base contains a fluorescent label. Read-out is accomplished by hybridizing the amplified DNA to an unlabelled microarray and determining the amount of fluorescent signal at particular known locations relative to controls. In general, such an assay would be multiplexed.

Additional embodiments of this assay include, but are not limited to, the following:

1) For a given polymorphism, e.g., an SNP, more than one 3' base-labeled oligonucleotide is used, with each different base having a different color label. Only those bases corresponding to polymorphic alleles present in the sample will be extended at any significant rate, and thus only colors corresponding to those bases will be significantly incorporated into the amplified DNA. Therefore, after hybridization, the colors present at an array site expected to hybridize to a particular product correspond to the polymorphism alleles present in the original sample. In this case, each allele and heterozygotes are distinguishable by the ratios of the amount of each color present, and are all clearly distinguishable from reaction failures, which have no or very little color present.

2) For hybridization to be specific to amplified product, it must depend at least in large part on sequences not contained in the labeled input primer. Specific hybridization may be accomplished in at least two ways. A) The amplicon may contain some sequence, preferably at least 10 bases, that is not contained in either of the two PCR primers, and hybridization to the array may depend on the presence of this sequence. Amplicons may be large, with reliable amplification of at least 5 kb being known in the art. Therefore it should always be possible to find a set of sufficiently non-cross-hybridizing sequences sufficiently close to a polymorphic site, e.g., an SNP site, so that specific arrays may be constructed. B) A set of pre-determined hybridization sites may be incorporated into the non-labeled primers for each amplicon, and these predetermined sites may be used as a basis for differential hybridization to an array. This method allows the use of standard arrays for many different polymorphism-scoring assays, through the incorporation of the same set of pre-determined hybridization sites into the unlabeled oligonucleotides of each different assay.

An advantage of method A is that it assures that only amplification products corresponding to the correct locus will be contribute to the hybridization signal. In practice, method B can be sufficiently specific, and can be justified by the cost advantage of using standard arrays. Methods A and B may also be used in combination in a single experiment.

3) Other types of fluorescent reporter configurations may be used. Arrays may be labeled with a fluor, and the read-out may be on the basis of FRET between the array and the amplicon. Oligonucleotides may be double-labeled with two fluors or a fluor and a quencher, and readout may depend on changes in fluorescence due to removal of one moiety.

Assay 3: Post-Amplification Readout Using Electrophoresis

This assay is similar to Assay 2, with a different readout mechanism. Amplifications are performed, preferably directly from genomic DNA, and the assay is read out by electrophoretic analysis with fluorescent detection. In general, this assay is performed by PCR amplification, where one of the primers has the polymorphic, e.g., a SNP site, at its 3' end, and that base contains a fluorescent label. Electrophoretic analysis is accomplished by capillary or gel electrophoresis instruments well known in the art, intended for fluorescent automated DNA sequencing or other types of fluorescent DNA fragment analysis. In general, such an assay would be multiplexed. Additional refinements are also possible and include, but are not limited to, the following:

1) For a given polymorphism, more than one 3' base-labeled oligonucleotide is used, with each different base having a different color label. Only those bases corresponding to polymorphic, e.g., SNP, alleles present in the sample will be extended at any significant rate, and thus only colors corresponding to those bases will be significantly incorporated into the amplified DNA. Therefore, upon electrophoretic analysis, the colors present at a position corresponding to the expected size of a particular product correspond to the polymorphic alleles present in the original sample. In this case, each allele and heterozygotes are distinguishable by the ratios of the amount of each color present, and are all clearly distinguishable from reaction failures, which have no or very little color present.

2) Multiple polymorphic sites, such as SNP sites, may be assayed in a single electrophoretic run by the simple expedient of adjusting the amplicon size so that each polymorphic site corresponds to a distinguishable amplicon size. This adjustment can be made by choosing the sequence of the unlabeled primer to correspond to sequences at various distances from the SNP site. In some instances, a particular primer sequence may be disfavored because of its potential for illegitimate hybridization; in this case, a different length can be chosen, or the strand of the labeled primer may be switched. A typical electrophoretic instrument such as the BaseStation (MJ Research, Waltham Mass.) can easily resolve fragments at four-base intervals to lengths greater than 1100 bases in 96 sample lanes simultaneously. If each lane contains alleles starting at 80 bases (so as to be separated from free dye breakdown products and primer-dimer artifacts) and continuing to 1100 bases, over 250,000 determinations cam be made in a four-hour run on a single instrument.

Assay Components

Oligonucleotides

Oligonucleotides used in the invention typically containing base-linked fluors and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.).

The primers for the amplification reactions are designed according to known algorithms. Typically, commercially available or custom software will use algorithms to design primers such that that annealing temperatures are close to melting temperature. Typically, the primers are at least 12 bases, more often 15, 18, or 20 bases in length. Primers are typically designed so that all primers participating in a particular reaction have melting temperatures that are within 5° C., and most preferably within 2° C. of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 μM to 0.5 μM.

The polymerase reactions are incubated under conditions in which the primers hybridize to the target sequences and are extended by a polymerase. As appreciated by those of skill in the art, such reaction conditions may vary, depending on the target sequence and the composition of the primer. The amplification reaction cycle conditions are selected so that the primers hybridize specifically to the target sequence and are extended. Exemplary PCR conditions for particular primer sets are provided in the examples.

In some cases, base-linked fluors are incorporated into the oligonucleotdies by post-synthesis modification of oligo-nucleotides that were synthesized with reactive groups linked to bases. One of skill will recognize that a large number of different fluorophores are available, including from commercial sources such as Molecular Probes, Eugene, Oreg. and other fluorophores known to those of skill in the art. For a general listing of useful fluorophores, see Hermanson, G. T., BIOCONJUGATE TECHNIQUES (Academic Press, San Diego, 1996). Thus, each probe will fluoresce at a different wavelength and can be individually detected without interference from the other probes.

Fluorescence-based assays can also rely for signal generation on fluorescence resonance energy transfer, or "FRET", according to which a change in fluorescence is caused by a change in the distance separating a first fluorophore from an interacting resonance energy acceptor, either another fluorophore or a quencher. Combinations of a fluorophore and an interacting molecule or moiety, including quenching molecules or moieties, are known as "FRET pairs." The mechanism of FRET-pair interaction requires that the absorption spectrum of one member of the pair overlaps the emission spectrum of the other member, the first fluorophore. If the interacting molecule or moiety is a quencher, its absorption spectrum must overlap the emission spectrum of the fluorophore. Stryer, L., *Ann. Rev. Biochem.* 47: 819–846 (1978); BIOPHYSICAL CHEMISTRY part II, Techniques for the Study of Biological Structure and Function, C. R. Cantor and P. R. Schimmel, pages 448–455 (W. H. Freeman and Co., San Francisco, U.S.A., 1980); and Selvin, P. R., *Methods in Enzymology* 246: 300–335 (1995). Efficient FRET interaction requires that the absorption and emission spectra of the pair have a large degree of overlap. The efficiency of FRET interaction is linearly proportional to that overlap. See Haugland, R. P. et al *Proc. Natl. Acad. Sci. USA* 63: 24–30 (1969). Typically, a large magnitude of signal (i.e., a high degree of overlap) is required. FRET pairs, including fluorophore-quencher pairs, are therefore typically chosen on that basis.

A variety of labeled nucleic acid hybridization probes and detection assays that utilize FRET and FRET pairs are known. One such scheme is described by Cardullo et al. *Proc. Natl. Acad. Sci. USA* 85: 8790–8794 (1988) and in Heller et al. EP 0070685. It uses a probe comprising a pair of oligodeoxynucleotides complementary to contiguous regions of a target DNA strand. One probe molecule contains a fluorescent label, a fluorophore, on its 5' end, and the other probe molecule contains a different fluorescent label, also a fluorophore, on its 3' end. When the probe is hybridized to the target sequence, the two labels are brought very close to each other. When the sample is stimulated by light of an appropriate frequency, fluorescence resonance energy transfer from one label to the other occurs. FRET produces a measurable change in spectral response from the labels, signaling the presence of targets. One label could be a "quencher," which in this application is meant an interactive moiety (or molecule) that releases the accepted energy as heat.

Solid Supports

Any solid support, including, but not limited to membrane filters, slides, microparticles and the like, may be used in the methods of the invention. In particular embodiments, microarrays are used. Labeled arrays, e.g., those used in assay 1, are constructed by attachment of separately-synthesized oligonucleotides using any of several attachment chemistries, below. Unlabeled oligonucleotides, e.g., those prepared for Assay 2, may be attached by such methods, and additionally may be synthesized directly in situ by various techniques. Such arrays are made, e.g., by Affymetrix (Santa Clara Calif.) and Rosetta Inpharmics (Kirkland Wash.).

Attachment Chemistries

Because probe oligonucleotides used, e.g., in Assay 1 must have free 3' ends, they cannot be synthesized on the surface where they will be used by conventional phosphoramidite chemistry, which results in the 3' end being attached to the substrate. Instead, they are synthesized separately, with a functional group, such as an amino, acrylic (Mosaic Technologies, Boston Mass.), or thiol group, on the 5' end. Appropriate surfaces with functional groups are readily available. For example, glass slides are conventionally available with aminosilane or poly-L-lysine coatings providing amino groups. Glass slides may be modified via silane chemistry to have a reactive vinyl group, and may be coupled to an oligonucleotide containing an acrylic group via radical vinyl polymerization, for instance in the presence of acrylamide monomers. Polystyrene beads are conventionally available with carboxyl groups on their surfaces. Other types of surface groups can be obtained through conventional chemical manipulations. These functional groups can be used to link the oligonucleotides to the surface through conventional chemistries. Preferably, the oligonucleotides are attached to the discrete surface locations.

Multiplexing

Multiplexing of PCR amplification is well known in the art. The reaction described herein can be highly multiplexed. Not to be bound by theory, the reactions can be highly multiplexed for the following reasons. First, unwanted, non-specific reaction products can be kept to a minimum by primer design, use of minimal primer concentration, and close control over reaction conditions. For example, primers are designed to have about the same $T_M$, usually within 10° C., often 5° C., or 2° C. The primers are also designed to avoid producing a PCR product by mispairing. The reaction is controlled to keep the annealing and extensions temperatures such that the primers do not prime at incorrect sites at a detectable level. Second, by incorporating element 6 of Assay 1, unwanted reaction products can be kept from substantial interference with the assay. For Assays 2 and 3, effective multiplexing may be increased by splitting an assay into several separate vessels, each with a different set of primers, and combining them for the purposes of read-out.

Polymerases

Polymerases are well-known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In E. coli, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases.

Polymerases with 3' to 5' exonuclease activity are used in the invention. These include family B polymerases such as *Pyrococcus* polymerases such as Pfu, Pho, Pab, Pko, Pgl etc. and *Thermococcus* polymerases such as Tli (Vent), which are sufficiently thermostable to be suitable for PCR. Family A polymerases that have error-correcting activity may also be used, e.g., Tth. Further, in some embodiments, non-thermostable polymerases may be used. For example, *E. coli* PolI has 3' to 5' exonuclease activitiy and could be used in an embodiment where the error correcting step is not performed at high temperatures.

In some embodiments, it is advantageous to use polymerases having enhanced processivity, "improved polymerases". Examples of these include those described in WO01/92501. These improved polymerases exhibit enhanced processivity due to the presence of a sequence-non-specific double-stranded DNA binding domain that is joined to the polymerase or the enzymatic domain of the polymerase). Often the binding domain is from a thermo-stable organism and provides enhanced activity at higher temperatures, e.g., temperatures above 45° C. For example, Sso7d and Sac7d are small (about 7,000 kd MW), basic chromosomal proteins from the hyperthermophilic archaea-bacteria *Sulfolobus solfataricus* and *S. acidocaldarius*, respectively (see, e.g., Choli et al., *Biochimica* et *Biophysica Acta* 950:193–203, 1988; Baumann et al., *Structural Biol.* 1:808–819, 1994; and Gao et al, *Nature Struc. Biol.* 5:782–786, 1998). These proteins bind DNA in a sequence-independent manner and when bound, increase the $T_M$ of DNA by up to 40° C. under some conditions (McAfee et al., *Biochemistry* 34:10063–10077, 1995). These proteins and their homologs are often used as the sequence-non-specific DNA binding domain in improved polymerase fusion proteins.

Often, in embodiments in which long PCR is necessary, improved polymerases are used. These polymerases can be used to obtain long, i.e., 5 kb, often 10 kb, or greater in length, PCR products. "Long PCR" using these improved polymerases can be performed using extension times that are reduced compared to prior art "long PCR" polymerase and/or polymerase mixtures. Extension times of less than 30 seconds per kb, often 15 seconds per kb, can be used to amplify long products in PCR reactions using the improved polymerases. Furthermore, these modified polymerases also exhibit increased sensitivity.

Prior-art non-error-correcting polymerases such as Taq polymerase are capable of amplifying DNA from very small input copy concentrations, such as, in the extreme, 10 copies per ml. However, because of the low fidelity of such polymerases, products cloned from such amplifications are likely to contain introduced mutations.

Prior-art error-correcting polymerases such as Pfu copy DNA with higher fidelity than Taq, but are not capable of amplifying DNA from small input copy concentrations. The hybrid error-correcting polymerases of the invention exhibit much higher processivity while retaining error-correcting activity and thereby provide both sensitivity and fidelity in amplification reactions.

Reactions

Typical reactions may be set up as follows:

Assay 1 : Genomic DNA from an individual to be tested is mixed with a PCR mixture containing an appropriate polymerase and one unlabelled primer pair for each locus to be tested. The reaction mixture is placed into a vessel and put into contact with surfaces to which probe oligonucleotides are attached. The combination of a vessel and surfaces for probe attachment can be satisfied in several ways: for instance, a standard plastic thermal cycling reaction vessel containing color-coded polystyrene beads to which probes are attached; or a glass slide with probes attached in discrete spots, and an appropriate chamber or cover for containing the reaction volume. The vessel is then thermally cycled to allow the PCR and assay to proceed.

Assays 2 and 3 : Genomic DNA from an individual to be tested is mixed with a PCR mixture containing an appropriate polymerase and one primer pair for each locus to be tested, where a primer pair consists of one labeled and one unlabeled primer. After amplification, all separate amplification tubes are combined, and the products are denatured and analyzed by the method of choice.

Reaction variations—At least some amplification may take place before the solution containing DNA to be tested is exposed to the surface with attached probe oligonucleotide. An amplification other than PCR, such as transcription-mediated amplification (TMA), strand displacement amplifcation (SDA), nucleic acid sequence-based amplification (NASBA), LCR, oligonucleotide ligation assay (OLA), etc., may be employed. In this case, concurrent amplification may not be used.

Readout—Fluorescence may be quantified in the discrete locations by any of several methods. Numerous commercially-available instruments, such as those manufactured by Axon Instruments (Foster City, Calif.) and Applied Precision (Issaquah, Wash.) can quantify fluorescence from spots on the surface of a flat substrate. Fluorescent-coded beads can be read using flow-cytometry-type instrumentation, such as that manufactured by Luminex (Austin, Tex.). Other optical properties besides color of fluorescent emissions can be used to distinguish reaction products—for instance, time-resolved fluorescence.

Interpretation—For the case where the query position of the probe contains a quencher, an increase in fluorescence, relative to a control, from a discrete location in a particular color indicates that the 3' nucleotide of the probe corresponding to that location and color does not match at least some of the amplicons present in the solution. For a homozygote for a particular SNP allele, the expected pattern is a large increase in fluorescence for each probe with a 3' mismatch. For a heterozygote, all probes are expected to have an increase in fluorescence, but those corresponding to the SNP alleles that are actually present will show a smaller increase in fluorescence due to the fact that the probes can be extended, and thus protected from nuclease activity, if they anneal to a matched amplicon.

All publications, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of non-critical parameters that could be changed or modified to yield essentially similar results.

Example 1

Modified Error-Correcting Enzymes are Superior to Unmodified Error-correcting Enzymes in Amplifying DNA from Low Copy Number Templates The efficiency with which modified and unmodified error-correcting polymerases can amplify products from small numbers of input template copies was tested using "real-time" PCR. PCR was performed in the presence of the double-stranded-DNA-specific fluorescent dye SYBR Green I (Molecular Probes, Eugene Oreg.) in a DNA Engine Opticon continuous fluorescence detection thermal cycling system (MJ Research, Waltham Mass.). A 57 bp portion of the human cytochrome P450 gene CYP2D6 (GenBank Accession # M33388, nucleotides 3265–3322) was amplified using primers F1 (forward) and R1 (reverse) from a template containing a perfect match to both primers. The number of thermal cycles required for the fluorescence to reach a threshold value (threshold cycle, or $C_t$) was recorded. The $C_t$ value represents the number of cycles required to generate a detectable amount of DNA. A "detectable" amount of DNA is at least 2 standard deviations, and usually 5 or more standard deviations above the background noise level. In the conditions employed in this example, a detectable amount corresponds to approximately 1 ng of DNA. An efficient polymerase may be able to produce a detectable amount of DNA in a smaller number of cycles by more closely approaching the theoretical maximum amplification efficiency of PCR. Accordingly, a lower $C_t$ value reflects a greater amplification efficiency for the enzyme. The enzymes tested were Pfu (Stratagene, La Jolla Calif.) and PfS, a fusion of Sso7d to the carboxy terminus of Pfu, as described in the co-pending U.S. application Ser. No. 09/870,353. Each enzyme was tested over a range of concentrations from 40 units/ml to 5 units/ml. PfS was found to require between ¼ and ⅟₁₀ as many units as Pfu for efficient amplification. Each enzyme was used in its optimal buffer.

Primer F1:  AGG CGC TTC TCC GTG       (SEQ ID NO:1)

Primer R1:  CTC CAG CGA CTT CTT GC    (SEQ ID NO:2)

Reaction conditions
20 µl reactions contained:
0.5×SYBR Green I
10 mM KCl (Pfu) or 50 mM KCl (PfS)
2 mM MgCl2
10 mM Tris-Cl, pH 8.75
200 mM each dNTP
300 µM each primer Enzyme and template amounts as listed below.

Thermal cycling conditions were:

| | |
|---|---|
| 1 | 94° C. 2 minutes |
| 2 | 94° C. 10 seconds |
| 3 | 60° C. 15 seconds |
| 4 | 72° C. 30 seconds, take fluorescence reading |
| 5 | Go to step 2, 45 cycles |
| 6 | 72° C. 10 minutes |

Table 1. Effect if enzyme type and amount in threshold cycle

TABLE 1

Effect of enzyme type and amount on threshold cycle

| Input Template Copy No. | $10^7$ | $10^6$ | $10^5$ | $10^4$ | $10^3$ | $10^2$ | 10 |
|---|---|---|---|---|---|---|---|
| PfS, Units/ml | | | | | | | |
| 40 | 16.3 | 20.5 | 23.0 | 26.3 | 29.5 | 30.5 | 33.1 |
| 20 | 16.9 | 20.5 | 22.4 | 26.1 | 29.6 | 26.5 | 35.0 |
| 10 | 17.1 | 20.0 | 21.7 | 26.0 | 29.4 | 32.2 | 34.5 |
| 5 | 20.2 | 23.8 | 24.6 | 31.0 | 34.2 | 43.3 | 41.2 |
| Pfu, Units/ml | | | | | | | |
| 40 | 16.1 | 21.9 | 22.7 | 27.2 | 29.5 | 35.6 | 37.0 |
| 20 | 26.6 | 28.6 | 35.7 | 36.0 | 45.7 | — | — |
| 10 | 25.4 | — | — | — | — | — | — |
| 5 | 40.2 | — | — | — | — | — | — |

PfS amplified the template with high efficiency at enzyme concentrations from 10–40 U/ml at all input DNA copy numbers, down to 10 copies. PfS showed slightly less efficient amplification at 5 U/ml. By contrast, Pfu only amplified the template efficiently at 40 U/ml, and even then, only down to an input copy number of 1000 copies. At lower enzyme or template concentrations, amplification was inefficient, and in many cases did not result in a detectable product generated within the 46 cycles of the experiment.

Example 2

The Error-Correcting Enzymes Pfu and PfS Efficiently Correct Mismatched Labeled Bases During PCR Amplification PCR was performed using a 3' base-labeled primer in conditions where it had either a perfect match with the template, or a 3' single-base mismatch with the template. Primer F2 was the base-labeled primer, with the same sequence as primer F1 except the 3' G (query position) is replaced with a C with a carboxyfluorescein (FAM) dye attached at the 5 position through a linker. $10^6$ copies of plasmid clones with either a G or a C in the polymorphic position were used as templates. The reverse primer, R2, was designed to produce a 475-base amplicon. Enzymes used were Taq Gold (ABI, Foster City Calif.), PfS, and Pfu. Six PCRs were performed, with all combinations of the three enzymes and two templates.

Conditions were similar to those from example 1. Taq Gold reactions used the commercially-supplied 2× master mix. 2× master mixes were also prepared for Pfu and PfS, which were each used at 20 U/ml.

Each 20 μl reaction contained:
7 μl ddH2O
2 μl 10× primers (final 0.3 μM each)
1 μl (10^6 copies/μl cut plasmid template DNA) 10 μl 2× master mix Cycling program:
1: 94° C. forever (insert sample plate while the block has reached 940° C., then skip to step 2.
2: 94° C. 2min
3: 96° C. 10 s
4: 55° C. 15 s
5: 74° C. 40 s
6: go to step 2 for 29 times
7: 72° C. for 10 min

```
Primer F2:   AGG CGC TTC TCC GTC(FAM)    (SEQ ID NO:3)
Primer R2:   ATG TCC TTT CCC AAA CCC AT  (SEQ ID NO:4)
```

Results:
FIG. 1 shows an aliquot of each reaction run on an agarose gel and stained with ethidium bromide. Products were produced in all reactions, though there was a lower yield for the mismatch condition with Taq and Pfu. The overall yield was highest with PfS.

Figure 2:
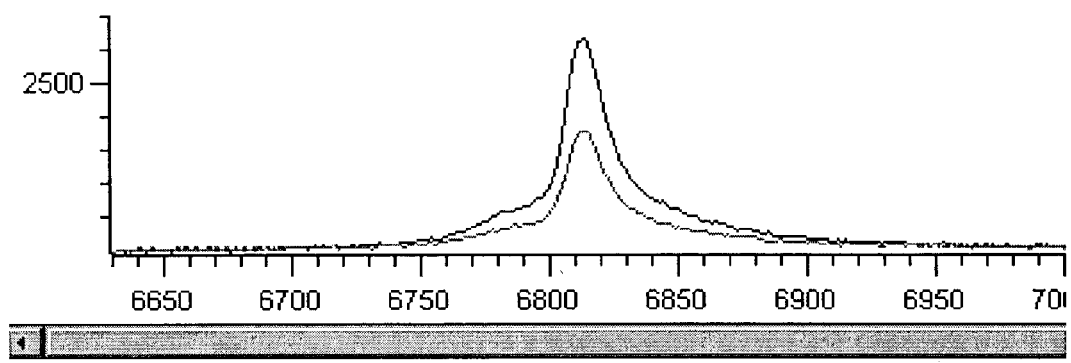
FIG. 2 shows fluorescent intensity traces (electropherograms) for Taq and PfS reactions.
Figure 2:
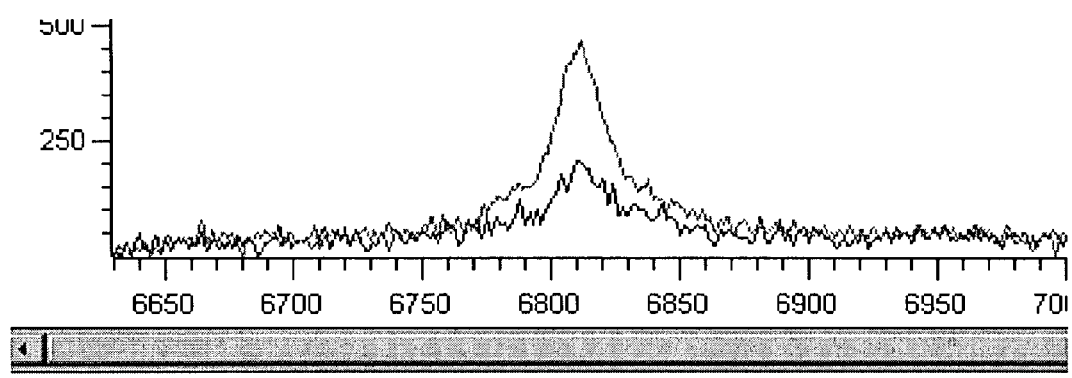
Figure 2:
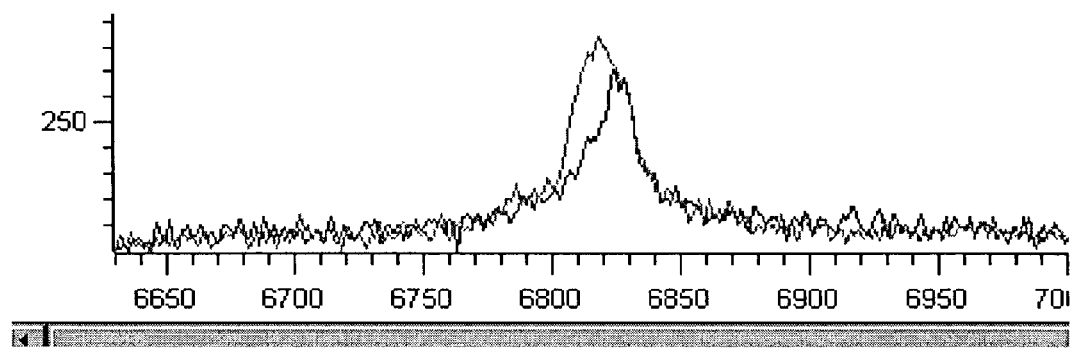

Products of the six reactions were diluted to equalize the concentrations, then equal amounts were loaded on six lanes of a BaseStation fluorescent electrophoretic analyzer. Results are shown in FIG. 2. Taq Polymerase produced a labeled band in both match and mismatch conditions, indicating that, as expected, the enzyme was not capable of correcting a mismatch, but simply extended the mismatched base. Both PfS and Pfu produced a labeled band in the matched condition, showing that they were capable of extending from the 3' end of the labeled base. However, both enzymes produced an essentially unlabeled band in the mismatch condition, demonstrating that they are capable of very efficiently correcting the 3' labeled base before extending the primer.

Example 3

PCR was performed using a 3' base-labeled primer in conditions where it had either a perfect match with the template, or a 3' single-base mismatch with the template. Two labeled primers were used: F2 and F3 were base-labeled, with the same sequence as primer F1 except the 3' G (query position) is replaced with a C with a carboxyfluorescein (FAM) dye attached at the 5 position through a linker o or a T labeled with Bodipy R6G (BR6G) (Molecular Probes, Eugene Oreg.) linked to the T methyl group via a 6-carbon linker. $10^6$ copies of plasmid clones with either a G or a C in the polymorphic position were used as templates. The reverse primer, R2, was designed to produce a 475-base amplicon. Enzymes used were Taq Gold (ABI, Foster City Calif.), PfS, and Pfu. Twenty seven PCRs were performed, with all combinations of the three enzymes, two primers singly and in combination, and two templates singly and in combination.

Primer F3 was poorly labeled (only about 7% of molecules were dye-labeled) so it was used at a higher concentration than primer F2 to compensate for that difference.

```
Primer F2:    AGG CGC TTC TCC GTC (FAM)   (SEQ ID NO:3)

Primer F3:    AGG CGC TTC TCC GTT (R6G)   (SEQ ID NO:5)

Primer R2:    ATG TCC TTT CCC AAA CCC AT  (SEQ ID NO:4)
```

Conditions were similar to those from example 1. Taq Gold reactions used the commercially-supplied 2× master mix. 2× master mixes were also prepared for Pfu and Pfs, which were each used at 20 U/ml.

Each 20 µl Reaction Contained:
7 µl ddH2O
2 µl 10× primers (final 0.1 µM F2, 1.5 µM F3, and 0.3 µM R2 each)
1 µl (10⁶ copies/µl cut plasmid template DNA) (cut template)
10 µl 2× master mix Cycling Program:
1: 94° C. forever (insert sample plate while the block has reached 94° C., then skip to step 2.
2: 94° C. 2 min
3: 96° C. 10 s
4: 55° C. 15 s
5: 74° C. 40 s
6: go to step 2 for 29 times
7: 72° C. for 10 min PCR products were analyzed electrophoretically on a BaseStation fluorescent electrophoretic analyzer (MJ Research, Waltham Mass.). Fluorescence intensity traces for each lane were baseline subtracted, but no attempt was made to perform a color separation deconvolution. Table 2 summarizes the results. The numbers presented in Table 2 are the heights of peaks corresponding to a 475-base fragment. If no peak was detectable, no number is given. Channel 1 is about twice as sensitive to FAM as BR6G, while channel 2 is about twice as sensitive to BR6G as FAM. So a pure peak of one dye will result in a peak in its corresponding channel and a peak of half that height in the other channel.

Results:

Although the results are somewhat skewed by the poor labeling of the T oligo and the corresponding compensation by concentration adjustment, it is clear that the assay works well. In particular, Table 2 shows that for the case where a mixture of the C and T primers is used, the reactions employing PfS can clearly distinguish between templates consisting of 100% A, 100% G, and a 50/50 mixture of A and G. These three cases correspond to a valuable use of the assay in distinguishing between two homozygotes and a heterozygote.

In FIG. 2, all three panels are electropherograms of reactions from Example 3 employing mixed C and T labeled primers. Channel 1 signal is in black and channel 2 signal is in grey. The top panel was from Lane 12, the reaction with G template, and channel 1 signal is double that from channel 2, indicating a pure C peak. The center panel was from Lane 15, the reaction with A template, and channel 2 signal is double that from channel 1, indicating a pure T peak. The bottom panel was from Lane 18, the reaction with mixed A and G template, and channel 1 and channel 2 signals are approximately equal, indicating a both a C and a T peak. Further, in the bottom pane, the channel 1 and 2 signals are not coincident, corresponding to a small mobility difference between the two dyes, further reinforcing the conclusion that both labeled peaks are present.

PfS performed much better that Pfu in this example, although it is expected that with a high input copy number and a sufficiently high enzyme concentration, Pfu would perform adequately.

TABLE 2

| Enzyme | Primer | Template | Channel 1 | Channel 2 | Base |
|---|---|---|---|---|---|
| Taq | C | G | 2000 | 1000 | C |
| Taq | T | G | | | |
| Taq | C + T | G | | | |
| Taq | C | A | 900 | 400 | C |
| Taq | T | A | 35 | 70 | T |
| Taq | C + T | A | 20 | 30 | T |
| Taq | C | G + A | 2000 | 1000 | C |
| Taq | T | G + A | | | |
| Taq | C + T | G + A | 40 | 80 | T |
| PfS | C | G | 3200 | 1800 | C |
| PfS | T | G | | | |
| PfS | C + T | G | 410 | 210 | C |
| PfS | C | A | 2800 | 1500 | C |
| PfS | T | A | 150 | 550 | T |
| PfS | C + T | A | 100 | 400 | T |
| PfS | C | G + A | 3000 | 1500 | C |
| PfS | T | G + A | 150 | 400 | T |
| PfS | C + T | G + A | 300 | 360 | C/T |
| Pfu | C | G | 1800 | 800 | C |
| Pfu | T | G | | | |
| Pfu | C + T | G | | | |
| Pfu | C | A | 760 | 360 | C |
| Pfu | T | A | | | |
| Pfu | C + T | A | | | |
| Pfu | C | G + A | 2000 | 1000 | C |
| Pfu | T | G + A | | | |
| Pfu | C + T | G + A | | | |

What is claimed is:

1. A method of identifying a polymorphism using an error-correcting assay, the method comprising:
   (a) contacting a target nucleic acid comprising a query sequence with a probe oligonucleotide in an assay under conditions in which the probe specifically hybridizes to the target nucleic acid, wherein the 3' nucleotide of the probe is a labeled query nucleotide and the probe is attached to a discrete surface location, wherein the attachment of the probe to the surface location permits the 3' nucleotide to participate in enzymatic reactions;
   (b) providing an error-correcting polymerase, wherein the error correcting polymerase is joined to a sequence non-specific nucleic-acid-binding domain that (i) binds to double-stranded nucleic acid, and (ii) enhances the processivity of the polymerase compared to an identical polymerase not having the sequence non-specific nucleic-acid-binding domain fused to it;

(c) incubating the assay under conditions in which the probe is extended by the polymerase, wherein the labeled query nucleotide is cleaved from the probe when mismatched with the query sequence; and (d) detecting the amount of probe in the discrete location that has been labeled, wherein the amount of labeled probe in the discrete location is indicative of the presence or absence of the polymorphism.

2. The method of claim 1, wherein the polymerase is a family B polymerase.

3. The method of claim 2, wherein the family B polymerase is a *Pyrococcus* polymerase.

4. The method of claim 1, wherein the polymerase is a family B polymerase.

5. The method of claim 4, wherein the polymerase is a *Pyrococcus* polymerase.

6. The method of claim 5, wherein the error-correcting polymerase is Pfu-Sso7d.

7. The method of claim 1, wherein the target nucleic acid is a PCR amplicon obtained using a PCR reaction performed with two unlabeled primers, wherein the query sequence is not present in either of the two primers.

8. The method of claim 7, wherein the target nucleic acid is obtained using a PCR reaction performed with two unlabeled primers, wherein the query sequence is not present in either of the two primers; and further, wherein the PCR reaction is contacted with the probe oligonucleotide during amplification.

9. The method of claim 8, wherein the oligonucleotide probe is complementary to a region in the amplicon that does not comprise the two primers.

10. The method of claim 1, wherein the discrete surface location is on a microarray.

11. The method of claim 1, wherein the 3' query nucleotide is labeled with a quencher.

12. The method of claim 1, further comprising a second probe oligonucleotide comprising a label at the 3' end.

13. A method of identifying a polymorphism using an error-correcting assay, the method comprising:

(a) contacting a target nucleic acid comprising a query sequence with an oligonucleotide probe under conditions in which the probe specifically hybridizes to the target nucleic acid, wherein the 3' nucleotide of the probe is a labeled query nucleotide;

(b) providing an error-correcting polymerase comprising a sequence non-specific nucleic-acid-binding domain that (i) binds to double-stranded nucleic acid, and (ii) enhances the processivity of the polymerase;

(c) incubating the assay under conditions in which the probe is extended by the polymerase thereby providing an extended product, wherein the labeled query nucleotide is cleaved from the probe when mismatched with the query sequence;

(d) providing a capture oligonucleotide attached to a discrete location and complementary to the extended product, (e) hybridizing the extended product to the capture oligonucleotide and (f) detecting the amount of label at the discrete location, wherein the amount of label at the discrete location is indicative of the presence or absence of the polymorphism.

14. The method of claim 13, wherein the 3' nucleotide of the probe is labeled with a fluorescent label.

15. The method of claim 13, wherein the capture oligonucleotide is in a microarray.

16. The method of claim 13, wherein the 3' nucleotide of the probe is labeled with a fluorescent quenching molecule.

17. The method of claim 16, further wherein the extended product is hybridized to a capture oligonucleotide that is labeled with a fluor.

18. The method of claim 13 wherein the polymerase is a family B polymerase.

19. The method of claim 13, wherein the family B polymerase is a *Pyrococcus* polymerase.

20. The method of claim 13, wherein the error-correcting polymerase is Pfu-Sso7d.

21. A method of identifying at least two polymorphisms using an error-correcting assay, the method comprising:

(a) contacting a target nucleic acid comprising at least two query sequences with at least two oligonucleotide probes under conditions in which the probes specifically hybridize to the target nucleic acid at different sites, wherein the 3' nucleotides of the probes are labeled query nucleotides, and further, wherein the labels are different;

(b) providing an error-correcting polymerase comprising a sequence non-specific nucleic-acid-binding domain that (i) binds to double-stranded nucleic acid, and (ii) enhances the processivity of the polymerase;

(c) incubating the assay under conditions in which the probes are extended by the polymerase thereby providing extended products, wherein the labeled query nucleotides are cleaved from the probes when mismatched with the query sequences;

(d) separating the extended products electrophoretically, and (e) detecting the amount of label in the extended products, wherein the amount of label in the extended products are indicative of the presence or absence of the polymorphisms.

22. The method of claim 21, wherein the polymerase is a family B polymerase.

23. The method of claim 22, wherein the family B polymerase is a *Pyrococcus* polymerase.

24. The method of claim 21, wherein the error-correcting polymerase is Pfu-Sso7d.

25. A method of identifying a polymorphism using an error-correcting assay, the method comprising:

(a) contacting a target nucleic acid comprising a query sequence with a probe oligonucleotide under conditions in which the probe specifically hybridizes to the target nucleic acid, wherein the 3' nucleotide of the probe is a labeled query nucleotide;

(b) providing an error-correcting polymerase comprising at least two heterologous domains, wherein a first domain that is a sequence-non-specific nucleic-acid-binding domain is joined to a second domain that is a polymerase domain, wherein the sequence non-specific nucleic-acid-binding domain:

(i) binds to double-stranded nucleic acid, and (ii) enhances the processivity of the polymerase compared to an identical polymerase not having the sequence non-specific nucleic-acid-binding domain fused to it;

(c) incubating the assay under conditions in which the probe is extended by the polymerase, wherein the labeled query nucleotide is cleaved from the probe when mismatched with the query sequence; and (d) detecting the amount of cleaved label or cleaved probe, wherein the amount of cleaved label or cleaved probe is indicative of the presence or absence of the polymorphism.

26. The method of claim 25, wherein the polymerase is a family B polymerase.

27. The method of claim 26, wherein the family B polymerase is a *Pyrococcus* polymerase.

28. The method of claim 25, wherein the error correcting polymerase is joined to a sequence non-specific nucleic-acid-binding domain that (i) binds to double-stranded nucleic acid, and (ii) enhances the processivity of the polymerase compared to an identical polymerase not having the sequence non-specific nucleic-acid-binding domain fused to it.

29. The method of claim 28, wherein the polymerase is a family B polymerase.

30. The method of claim 29, wherein the polymerase is a *Pyrococcus* polymerase.

31. The method of claim 30, wherein the error-correcting polymerase is Pfu-Sso7d.

* * * * *